United States Patent [19]

Martino et al.

[11] Patent Number: 5,288,493
[45] Date of Patent: Feb. 22, 1994

[54] SKIN CARE COMPOSITIONS WITH IMPROVED RUB-OFF RESISTANCE

[75] Inventors: Gary T. Martino, Plainsboro; Dinesh C. Patel, Holmdel, both of N.J.; Jacob J. Guth, Upper Black Eddy, Pa.

[73] Assignee: National Starch and Chemical Investment Holding Corporation, Wilmington, Del.

[21] Appl. No.: 10,094

[22] Filed: Jan. 28, 1993

Related U.S. Application Data

[63] Continuation of Ser. No. 703,431, May 17, 1991, abandoned.

[51] Int. Cl.$^5$ .......... A61K 9/107; A61K 9/12
[52] U.S. Cl. .......... 424/401; 424/43; 424/59; 424/78.02; 424/78.03; 424/78.05; 424/78.06; 424/78.07; 514/937; 514/957
[58] Field of Search .......... 424/401, 43, 78.02, 424/59; 514/937, 957

[56] References Cited

U.S. PATENT DOCUMENTS

| | | | |
|---|---|---|---|
| 3,639,572 | 2/1972 | Heinrich et al. | 424/63 |
| 3,927,199 | 12/1973 | Micchelli et al. | 424/47 |
| 3,927,203 | 12/1975 | Seymour et al. | 424/61 |
| 4,057,624 | 11/1977 | Hase et al. | 424/78 |
| 4,128,634 | 12/1978 | Hase et al. | 424/81 |
| 4,172,122 | 10/1979 | Kubik et al. | 424/59 |
| 4,192,861 | 3/1980 | Micchelli et al. | 424/47 |
| 4,423,031 | 12/1983 | Murui et al. | 424/63 |
| 4,445,521 | 5/1984 | Grollier | 424/70 |
| 4,552,755 | 12/1985 | Randen | 424/81 |
| 4,842,852 | 6/1989 | Nowak, Jr. et al. | 424/71 |

FOREIGN PATENT DOCUMENTS 1952721 9/1970 Fed. Rep. of Germany ...... 424/401

*Primary Examiner*—Thurman K. Page
*Assistant Examiner*—Raj Bawa
*Attorney, Agent, or Firm*—Eugene Zagarella, Jr.

[57] ABSTRACT

Skin care compositions, such as creams and lotions, wherein improved rub-off resistance is attained by including an effective amount of a copolymer comprising:

a) 10-75% by wt. of a $C_1$ to $C_{18}$ alkyl acrylate/methacrylate, b) 10-70% by wt. of $C_1$ to $C_{18}$ N-substituted alkyl acrylamide, and c) 5-40% by wt. of unsaturated carboxylic acid having 3 to 5 carbon atoms.

22 Claims, No Drawings

SKIN CARE COMPOSITIONS WITH IMPROVED RUB-OFF RESISTANCE

This application is a continuation of application Ser. No. 07/703,431, filed May 17, 1991, now abandoned.

BACKGROUND OF THE INVENTION

This invention is directed to skin care compositions for application to the skin wherein improved rub-off resistance is attained.

The use of skin care products, often described as cosmetic or health care products, is a large and continuously growing consumer market. These products which include creams and lotions as well as various powders, sprays and other topical skin products must satisfy a number of different physical and chemical properties while imparting one or more attributes of beauty, health and comfort. Some of the properties that skin care products are concerned with include stability, compatibility, insensitivity (non-irritating) to skin, ease of application, aesthetics or appearance, toxicological and other health and safety considerations, effectiveness, fragrance or odor, moisturization and water-resistance. In view of the varying needs and types of application, it is easy to understand why many similar products exist and why no one product can meet all of the different requirements.

One area of interest for many skin care products is the ability of the product to resist physical rub-off or prevent physical removal of the active ingredients from the skin thus obtaining extended effectiveness. While many of these products are directly or indirectly concerned with the property of rub-off resistance, there still is the need to provide skin care compositions which, while satisfying the many chemical and physical needs, have significantly improved rub-off resistance.

SUMMARY OF THE INVENTION

This invention relates to skin care compositions which contain selected copolymers of acrylates/methacrylates, N-substituted acrylamides and unsaturated carboxylic acid and which exhibit improved rub-off resistance after application to the skin.

More particularly, this invention is directed to skin care compositions such as creams and lotions, wherein improved rub-off resistance is attained by including an effective amount of a copolymer comprising:
a) 10-75% by wt. of a $C_1$-$C_{18}$ alkyl acrylate/methacrylate;
b) 10-70% by wt. $C_1$-$C_{18}$ N-substituted alkyl acrylamide; and
c) 5-40% by wt. of an unsaturated carboxylic acid having 3 to 5 carbon atoms;
wherein all percentages total 100%.

DETAILED DESCRIPTION OF THE INVENTION

The use of selected copolymers of acrylates/methacrylates, N-substituted acrylamides and unsaturated carboxylic acid in skin care formulations in accordance with this invention provides improved rub-off resistance. The term rub-off resistance as used herein refers to physical abrasion such as rubbing the human skin with the hands or clothes or other physical interaction. It can also be described as the ability to hold active ingredients on the skin or prevent the removal of active ingredients from the skin by abrasion or other physical interaction. One way used to evaluate rub-off resistance is by determining the substantivity value of a composition using the test described below in the examples. The substantivity value or percent substantivity is the amount or percentage of the subject test composition remaining on the skin following a standard physical interaction or rub-off procedure. Skin care composition containing the selected copolymers of this invention have a substantivity value of at least 30 and preferred compositions have a substantivity value of at least 40 and more preferably at least 50.

The copolymers used in providing the improved rub-off resistance in skin care compositions involve three components, i.e., a) an acrylate/methacrylate, b) an N-substituted acrylamide and c) an unsaturated carboxylic acid. More particularly the copolymers comprise a) from about 10-75% by weight of $C_1$ to $C_{18}$, preferably $C_3$ to $C_8$ alkyl acrylate/methacrylate; b) from about 10 to 70% by weight of $C_1$ to $C_{18}$, preferably $C_4$ to $C_{10}$ N-substituted alkyl acrylamide and c) from about 5 to 40% by weight of unsaturated carboxylic acid of 3 to 5 carbon atoms preferably acrylic or methacrylic acid, wherein the percentages total 100%. Preferably, these copolymers comprise 30 to 60% by weight of the acrylate/methacrylate, 15 to 60% by weight of the acrylamide and 10 to 25% by weight of the carboxylic acid. More preferably the acrylamide will comprise 20 to 40% by weight of the copolymer and even more preferably 25 to 35% by weight. This copolymer is soluble in alcohols and other solvents used in cosmetic formulations and while insoluble in water can become soluble or dispersible by neutralization with appropriate alkaline material. These copolymers can therefore be formulated into the oil phase or aqueous phase of emulsions. Depending on the type and degree of neutralization and solubilization, the copolymers can be made suitable for use in many different skin care media.

The copolymers described above can be used in different skin care formulations to impart rub-off resistance. The term "skin care" cosmetic formulation or product as used throughout this application refers to products which are applied or treated to the human skin for beauty, health and comfort type purposes. Products falling into this category include creams and lotions such as skin conditioners, moisturizers, sunscreens and various facial and other body creams and lotions. They also include solid or stick type products such as lipstick as well as sprays, powders and other topical skin products which are applied to the skin for these same purposes of beauty, health and comfort.

The skin care compositions of this invention may involve different skin care media or systems and will comprise a suitable vehicle or base for the composition. This vehicle may be an emulsion, an oil base, an aqueous system, a solvent system or a combination of aqueous and solvent systems.

The emulsions are the preferred vehicle or base for the skin care compositions of this invention and products of this type include the skin care creams and lotions. These emulsions which comprise water-based and oil-based phases, may be oil-in-water emulsions having oil as the dispersed phase and water as the continuous phase or they may be water-in-oil emulsions with water dispersed in oil, which is the continuous phase. The oil phase, which may comprise from about 10 to 90% by weight of the composition, is typically made up of cosmetically acceptable or conventional oily substances that are soluble in this phase, such as oils, waxes and emulsifiers. Compounds which can be included in the oil phase are typically mineral, animal and vegetable oils and fats, synthetic esters or fatty acids with aliphatic alcohols, higher fatty alcohols, waxes, so called mineral fats and oils, such as paraffin oil, petrolatum, ceresin, silicone oils and silicone fats. The water phase may comprise from about 10 to 90% by weight of the composition and this will include water and water soluble components such as alkalis, alkanolamines, polyhydric alcohols and preservatives. These emulsions include one or more emulsifiers which usually are contained in the oil phase but in some instances, depending on the type, may be in the water phase. Emulsifiers, which may be ionic or nonionic are well known and constitute a large group of conventional and commercially available products. They are often characterized by their hydrophilic-lipophilic balance (HLB). Oil-in-water (O/W) emulsifying agents typically have an HLB of more than 6.0 and produce emulsions in which the continuous phase is hydrophilic and such emulsions are generally dispersible in water. Emulsifiers of this type include PEG 300 distearate, sorbitan monolaurate and triethanolamine stearate. Water-in-oil (W/O) emulsifiers usually have an HLB of less than 6.0, preferably below 5, and produce emulsions in which the continuous phase is lipophilic. Such emulsifiers include, lanolin alcohols, ethylene glycol monostearate, sorbitan monooleate and PEG 200 dilaurate. Emulsifiers with HLB's of between 5 and 7 may function as either W/O or O/W emulsifiers depending on how they are used.

The amount of emulsifier used in the emulsions of this invention can vary depending on the system and typically will be an effective emulsifying amount. More particularly, the amount of emulsifier can vary from about 0.1 to 25% by weight of the composition and preferably from about 1 to 10%.

Various other ingredients and additives may be included in one or both of the oil and water phases in the cosmetic skin care emulsions described above. This includes emollients, humectants, thickening agents, UV-light inhibitors, preservatives, pigments, dyes, colorants, perfumes and fragrances, antiseptics, antifungal, antimicrobial and other medicaments and solvents. Effective amounts of one or more of these and other active and functional ingredients is generally used and this can total from about 0.1 to 25% by weight of the composition and more particularly from about 0.1 to 15%.

Another type of skin care composition is the solid or liquid products using an oil base in combination with the selected copolymer of this invention. The oil base is essentially comprised of oils, fats and wax materials of the type described above in reference to emulsions and include any of the conventional and cosmetically acceptably oily substances known and used in cosmetic and health care related products for skin care. These oil base materials generally will comprise from about 65 to 99.8% by weight of the skin care product and more particularly from about 70 to 99.7%. Various other ingredients and additives similar to those described above in emulsion compositions may be included in these products.

Other skin care compositions using the selected copolymers in accordance with this invention involve aqueous or solvent systems wherein the added components are soluble or dispersible therein. The aqueous system will comprise the selected copolymers, additives and active and functional ingredients, optionally a propellant and the balance water. Generally, an aqueous system will comprise from about 25 to 99.8% by weight water, preferably 50 to 80%, from about 0.1 to 10% by weight of copolymer, preferably 0.3 to 5%, from about 0.1 to 25% by weight of additives and ingredients, preferably 0.1 to 15% and from about 0 to 50% by weight of propellant, preferably 0 to 30%. Compositions of this type include the topical sprays and products containing fragrances and antimicrobial agents.

The topical sprays include the aerosol sprays or products containing a propellant. While any of the known propellants may be used in the compositions of this invention, preferred propellants included the non-halogenated hydrocarbons, particularly the lower boiling hydrocarbons such as $C_3$–$C_6$ straight and branched chain hydrocarbons, i.e., propane, butane, isobutane and mixtures thereof. Other preferred propellants include the ethers, such as dimethyl ether, hydrofluorocarbon and the compressed gases such as $N_2$ and $CO_2$.

The use of a solvent system as the vehicle or base involves other skin care compositions containing the selected copolymer in order to provide rub-off resistance. The solvent system will comprise the selected copolymers, additives and active and functional ingredients, optionally a propellant and the balance solvent. The solvent may be any of the known organic solvents which may solubilize or disperse components of the skin care composition and more particularly aliphatic alcohols, esters, ethers, ketones, amines and hydrocarbons including the aromatic, nitrated and chlorinated hydrocarbons. Particularly preferred organic solvents are the lower aliphatic alcohols such as the $C_{1-3}$ alcohols and especially ethanol. Generally the solvent system will comprise from about 25 to 99.8% by weight of solvent, preferably 50 to 80%, from about 0.1 to 10% by weight of copolymer, preferably 0.3 to 5%, from about 0.1 to 25% by weight of additives and ingredients, preferably 0.1 to 15% and from about 0 to 75% by weight of propellant, preferably 0 to 35%.

The additives and other ingredients which may be included in either the aqueous or solvent based systems are the same as those described above for the emulsion and oil based systems. The propellants which may be included in the solvent system are the same as those described above for the aqueous systems. Additionally, a mixture of the aqueous and solvent systems may be used wherein water and solvent, especially alcohols are combined along with the components, i.e., copolymer, additives and propellant. Such a composition will comprise 25 to 99.8% by weight of a combination or water and solvent, preferably 50 to 80% along with the components as described above.

The acrylate or methacrylate/acrylamide/acid copolymers used in this invention will comprise from about 0.1 to 10% and preferably about 0.3 to 5% by weight of the cosmetic skin care composition. This copolymer is soluble in organic materials such as alcohols and is insoluble in water, but may become water dispersible/soluble through neutralization of its carboxyl groups with an alkaline material such as triethanolamine, 2-amino-2-methyl-1-propanol, sodium, ammonium and potassium hydroxide. Solubilization in the oil phase is accomplished with a polar fatty material such as stearic acid or isocetyl alcohol and may be enhanced by using a long chain amine such as stearyl dimethylamine or lauryl amido dipropylamine for neutralization.

Preparation of the cosmetic skin care emulsion compositions typically involves adding the oil soluble components in one vessel and heating to, e.g., 75° to 80° C. and combining the water soluble components in another vessel and heating to e.g., 75° to 80° C. Depending on whether O/W or W/O emulsion are being prepared, the warmed inner phase is then slowly added to the outer phase with agitation.

The following examples further illustrate the embodiments of this invention. In the examples all parts and percentages are given by weight and all temperatures in degrees Celsius unless otherwise noted.

EXAMPLE I

The acrylate/methacrylate, acrylamide, acid copolymers used in the skin care compositions of this invention are prepared in the following illustrative and typical polymerization method.

A reaction vessel equipped with a condenser and mechanical agitation means was charged with 51 parts of isobutyl methacrylate, 30 parts of N-substituted t-octyl acrylamide, 19 parts of acrylic acid, 2.0 parts of free radical initiator and 100 parts of ethanol. The contents were heated to the reflux temperature of the system and held there for a period of six hours, whereupon an additional 1.0 part of the initiator was added thereto. The system was then held at reflux for an additional four hours and the reaction then cooled to 30° C. and the polymer recovered by standard separation means.

This copolymer designated A along with other similar copolymers designated B to H were used in formulating the cosmetic skin care products illustrated in the following examples. The copolymers B to H had the following compositions:

Copolymer B—65% isobutyl methacrylate, 10% t-octylacrylamide, 25% acrylic acid
Copolymer C—15% isobutyl methacrylate, 60% t-octylacrylamide, 25% acrylic acid
Copolymer D—40% isobutyl metacrylate, 30% t-octylacrylamide, 30% methacrylic acid
Copolymer E—10% butyl acrylate, 35% methyl methacrylate, 30% t-octylacrylamide, 25% acrylic acid
Copolymer F—45% isobutyl methacrylate, 30% t-butylacrylamide, 25% acrylic acid
Copolymer G—35% isobutyl methacrylate, 30% t-octylacrylamide, 35% acrylic acid
Copolymer H—25% isobutyl methacrylate, 70% t-octylacrylamide, 5% acrylic acid

EXAMPLE II

The copolymers described in Example I were formulated into cosmetic lotions in the following manner.

An oil phase (Phase A) and a water phase (Phase B) having the following ingredients were prepared:

| | Parts by weight |
|---|---|
| PHASE A | |
| Mineral Oil #10 | 10.0 |
| Octyl palmitate | 2.0 |
| Stearic acid | 4.0 |
| Glycerol stearate | 3.0 |
| PEG-40 stearate | 1.0 |
| Dimethicone copolyol | 1.0 |
| Lanolin Oil | 0.5 |
| PHASE B | |
| Deionized H$_2$O | 74.75 |
| Triethanolamine (99%) | 1.30 |

The ingredients of Phase A were combined and heated to 80° C. In a separate vessel, the ingredients of Phase B were added and mixed and while maintaining agitation, 1.0 part of the selected copolymer A or C to H was added slowly. This phase was then heated to 50° C. and 0.25 part of a thickener, carbomer 934, a product of B. F. Goodrich, added slowly while heating was continued to 80° C. When each portion, i.e., Phase A and B was uniform they were combined, mixed and cooled to 40° C. A preservative, 1.0 part of Germaben II E, a product of sutton Laboratories, and 0.2 part of a fragrance were then added and the formulation cooked to room temperature. Note copolymer B was added to the same formulation but to the oil phase.

Each formulation was then tested for rub-off resistance using the following method:

TEST METHOD FOR DETERMINING RUB-OFF RESISTANCE

Equipment

Glass plates - jig
Glass slides
20 mil draw down bird
Analytical balance
675 g weighted block

PROCEDURE

1. Prepare glass plate jig by gluing glass slides across bottom to support test slides.
2. Weigh four glass slides.
3. Place four test slides in center of glass plate against stationary slides—place additional slides on sides and across tops of test slides.
4. Draw down 20 mil (1 mil = 1/1000 inch) wet film on the four pre-weighed slides. Allow to dry for one hour.
5. Take weight of slides.
6. Slides were wiped with weighted blocks under closely controlled conditions.
7. Re-weigh slides.

% SUBSTANTIVITY

A Weight of slide with sample—weight of slide = Initial Sample Weight
B Weight of slide with sample after wipe—weight of slide = Weight of Sample After Wipe $$\% \text{ Substantivity} = \frac{\text{Weight of Sample After Wipe } (B)}{\text{Initial Sample Weight } (A)} \times 100$$

An average was taken of the four samples and reported as % Substantivity for each sample evaluated.

The % substantivity or the amount of composition remaining after rub-off, i.e., rub-off resistance was determined for each of the sample cosmetic formulations containing copolymers A to H and a control composition containing no copolymer and the results given below.

| Sample-copolymer | % Substantivity |
|---|---|
| Control | 10.6 |
| A (30% acrylamide) | 64.2 |
| B (10% acrylamide) | 42.6 |
| C (60% acrylamide) | 51.9 |
| D (30% acrylamide) | 52.4 |
| E (30% acrylamide) | 83.4 |
| F (30% acrylamide) | 73.4 |
| G (30% acrylamide) | 70.9 |
| H (70% acrylamide) | 32.3 |

As can be observed, all the formulations gave better rub-off resistance or % substantivity then the control which contained no polymer. Additionally, all samples containing greater then 10% to less than 70% of the acrylamide component had especially good % substantivity values.

EXAMPLE III

In order to further evaluate the rub-off resistance properties of cosmetic skin compositions of the invention, a test procedure using the reduction of TEWL (transepidermal water loss) was used. This procedure where the cosmetic formulation of this invention, containing copolymer A, and a control sample, without polymer, were applied to skin of human participants and the reduction in TEWL determined under test conditions described below. The formulations for copolymer A and the control were those described in Example II.

Test Procedure

Eight sections, each $3 \times 3$ cm were marked off on the forearms of each of the participants.

TEWL measurements were made directly on each section by means of a SERVO-MED Model EP-1 evaporimeter.

Using a microsyringe, 27 mg of the test formula was applied to each of four squares; 27 mg of the control formula was applied to the other four squares. Formulas were spread uniformly and allowed to dry 5 minutes at 20° C. and 25% R.H.

Four sites (2 control and 2 test) were wiped with paper napkins under very closely controlled conditions of pressure applied, rate, etc. The remaining four sites were left undisturbed. After an additional one hour equilibration time at 21° C. and 25% R.H., TEWL was measured at each of the test sites once again.

Reduction in TEWL was calculated for each of the following test conditions:
Test patch without wipe
Test patch with wipe
Control patch without wipe
Control patch with wipe The following equation was used in each determination:

$$\% \text{ TEWL Reduction} = \frac{\text{TEWL }(B) - \text{TEWL }(A)}{\text{TEWL }(B)} \times 100$$

Where:
TEWL(A)=TEWL of treated skin after application
TEWL(B)=TEWL of treated skin before application

| Sample Applied | Results: Mean TEWL Reduction (%) | |
|---|---|---|
| | Unwiped | Wiped |
| Control (without Polymer) | 16.3% | 8.4% |
| Formulation with copolymer A | 14.0% | 15.4% |

These results show that the sample containing the copolymer, exhibited virtually no change in TEWL after wiping, as compared with the control indicating that much of the active ingredients used to reduce TEWL had been retained by the copolymer A sample. In other words there was less rub-off in the A formulation since the degree of reduction in TEWL was virtually unchanged after rub-off.

EXAMPLE IV

Rub-off resistance was evaluated for a topical spray cosmetic composition. This composition which was an antifungal powder spray, sold under the tradename Tinactin to which 2% by weight of copolymer A described in Example I was added. Tinactin is a product available from Schering Plough and comprises a propellant (A-46/57%), alcohol (SDA-40/14%), an active antifungal ingredient (tolnaftate 1%), a preservative (BHT) and talc. The sample composition containing copolymer A and a control without polymer were tested for rub-off resistance using the following test procedure:

TEST PROCEDURE FOR RUB-OFF RESISTANCE OF TOPICAL SPRAYS

Equipment

Wool swatches ($3 \times 3$ inches)
Masking Tape
Analytical Balance
675 g Weight

Procedure

1. Prepare wool swatches by framing with masking tape, covering approximately 1/8" of swatch. Weight swatch (Initial Weight).
2. Tape swatch to vertical surface.
3. spray swatch for 3 seconds from a distance of 10 inches (making sure swatch is at center of spray pattern).
4. Allow swatch to dry for 5 minutes. Re-weigh swatch (Spray Weight).
5. Tape swatch to horizontal surface (making sure to only tape down the framed area to avoid removing wool).
6. Tape second wool swatch on 675 g weight.
7. Draw down the weighted swatch across the sprayed swatch using even, slow speed.
8. Remove swatch from horizontal surface and re-weigh (Final Weight).

$$\text{Calculations: } \frac{\text{Final Weight} - \text{Initial Weight}}{\text{Spray Weight} - \text{Initial Weight}} \times 100 = \% \text{ Substantivity}$$

Eight runs were tested for each of the samples, i.e., with copolymer A and the control without copolymer. The results show the spray composition containing copolymer A increased the % substantivity from 55 for the control to 95% indicating the significant rub-off resistance provided by the copolymer containing sample.

EXAMPLE V

A skin care composition with rub-off resistance containing copolymer A, as described in Example I, was formulated (hand and body moisturizer) and had the following ingredients:

| | Parts by weight |
|---|---|
| PHASE A | |
| Mineral Oil #10 | 7.0 |
| Octyl palmitate | 2.0 |
| Stearic acid | 3.5 |
| Glycerol stearate | 3.0 |

| | Parts by weight |
|---|---|
| PEG-40 stearate | 1.0 |
| Dimethicone copolyol | 1.0 |
| Lanolin oil | 0.5 |
| PHASE B | |
| Deionized H$_2$O | 76.6 |
| Triethanolamine | 1.3 |
| Glycerin | 2.0 |
| Copolymer A | 1.0 |

Additional ingredients, i.e., 0.2 part of Carbomer 934, 1.0 part of Germaben II E and 0.2 part of a fragrance were added to the formulation in a similar manner as described in Example II.

EXAMPLE VI

Another skin care composition containing copolymer A, as described in Example I, was formulated (dry skin lotion) and had the following ingredients:

| | Parts by weight |
|---|---|
| PHASE A | |
| Cetyl alcohol | 2.0 |
| Octyl palmitate | 2.0 |
| Tridecyl neopentanoate | 4.0 |
| Mineral Oil #7 | 1.0 |
| Dimethicone | 1.0 |
| Ceteth-20 (ICI Americas, Inc.) | 1.0 |
| Laureth-4 (ICI Americas, Inc.) | 1.0 |
| PHASE B | |
| Deionized H$_2$O | 81.5 |
| Carbomer 940 | 0.5 |
| Copolymer A | 1.0 |
| Glycerin | 3.0 |
| Triethanolamine (99%) | 1.0 |

Additional ingredients, i.e. 1.0 part of Germaben II E, and a small effective amount of fragrance were added to the formulation in a similar manner as described in Example II.

What is claimed is:

1. In a skin care composition having a vehicle comprising:
   i) an emulsion,
   ii) an oil base,
   iii) an aqueous system,
   iv) a solvent system, or
   v) a mixture of aqueous and solvent systems,
wherein the aqueous system comprises from about 25 to 99.8% by weight water, from about 0.1 to 25% by weight of additives and ingredients, and from about 0 to 50% by weight of a propellant, and wherein the solvent system comprises from about 25 to 99.8% of organic solvent selected from the group consisting of aliphatic alcohols, esters, ethers, ketones, amines and hydrocarbons, from about 0.1 to 25% by weight of additives and ingredients, and from about 0 to 75% by weight of a propellant, the improvement comprising providing improved rub-off resistance by adding from about 0.1 to 10% by weight of a copolymer consisting essentially of:
   a) about 10 to 75% by weight of C$_1$ to C$_{18}$ alkyl acrylate or methacrylate,
   b) about 10 to 70% by weight of C$_1$ to C$_{18}$ N-substituted alkyl acrylamide, and
   c) about 5 to 40% by weigh of unsaturated carboxylic acid having 3 to 5 carbon atoms.

2. The composition of claim 1 wherein the additives and ingredients are selected from the group consisting of emolients, humectants, thickening agents, UV-light inhibitors, preservatives, pigments, dyes, colorants, perfumes and fragrances, antiseptics, antifungal and antimicrobial agents, and the propellant is selected from the group consisting of non-halogenated hydrocarbons, ethers, hydrofluorocarbon and compressed gases.

3. The composition of claim 1 wherein the composition has a substantivity value of at least 30.

4. The composition of claim 1 wherein the acrylate or methacrylate has a C$_3$ to C$_8$ alkyl group, the acrylamide is C$_4$ to C$_{10}$ N-substituted alkyl acrylamide and the acid is acrylic or methacrylic acid.

5. The composition of claim 4 wherein the copolymer consists essentially of about 30 to 60% by weight of the acrylate or methacrylate, about 15 to 60% by weight of the acrylamide and about 10 to 25% by weight of the acid component.

6. The composition of claim 5 wherein the copolymer consists essentially of isobutylmethacrylate, t-octylacrylamide and methacrylic acid.

7. The skin care composition of claim 1 wherein the vehicle comprises an emulsion of about 10 to 90% by weight of an oil phase and about 10 to 90% by weight of a water phase.

8. The composition of claim 7 wherein the composition has a substantivity value of at least 30.

9. The composition of claim 7 wherein the acrylate or methacrylate has a C$_3$ to C$_8$ alkyl group, the acrylamide is C$_4$ to C$_{10}$ N-substituted acrylamide and the acid is acrylic or methacrylic acid.

10. The composition of claim 9 wherein the copolymer consists essentially of about 30 to 60% by weight of the acrylate or methacrylate, about 15 to 60% by weight of the acrylamide and about 10 to 25% by weight of the acid component.

11. The composition of claim 10 wherein the copolymer consists essentially of isobutylmethacrylate, t-octylacrylamide and methacrylic acid.

12. The composition of claim 10 wherein the acrylamide component of the copolymer is present in an amount of from about 20 to 40% by weight.

13. In the method of treating skin with a skin care composition, the improvement comprising providing increased rub-off resistance by using the composition of claim 1 as the skin care composition.

14. The method of claim 13 wherein the additives and ingredients are selected from the group consisting of emollients, humectants, thickening agents, UV-light inhibitors, preservatives, pigments, dyes, colorants, perfumes and fragrances, antiseptics, antifungal and antimicrobial agents, and the propellant is selected from the group consisting of non-halogenated hydrocarbons, ethers, hydrofluorocarbon and compressed gases.

15. The method of claim 13 wherein the copolymer consists essentially of an acrylate or methacrylate having a C$_3$ to C$_8$ alkyl group, a C$_4$ to C$_{10}$ N-substituted alkyl acrylamide and acrylic or methacrylic acid, and wherein the composition has a substantivity value of at least 30.

16. The method of claim 15 wherein the copolymer consists essentially of about 30 to 60% by weight of the acrylate or methacrylate, about 15 to 60% by weight of the acrylamide and about 10 to 25% by weight of the acid component.

17. The method of claim 13 wherein the vehicle comprises an emulsion of about 10 to 90% by weight of an oil phase and about 10 to 90% by weight of a water phase.

18. The method of claim 17 wherein the copolymer consists essentially of an acrylate or methacrylate having a $C_3$ to $C_8$ alkyl group, a $C_4$ to $C_{10}$ N-substituted alkyl acrylamide and acrylic or methacrylic acid, and wherein the composition has a substantivity value of at least 30.

19. The method of claim 18 wherein the copolymer consists essentially of about 30 to 60% by weight of the acrylate or methacrylate, about 15 to 60% by weight of the acrylamide and about 10 to 25% by weight of the acid component.

20. The method of claim 19 wherein the acrylamide component is present in an amount of from about 20 to 40% by weight.

21. The method of claim 20 wherein the copolymer consists essentially of isobutylmethacrylate t-octylacrylamide and methacrylic acid.

22. The method of claim 19 wherein the acrylamide component is present in an amount of from about 25 to 35% by weight.

* * * * *